United States Patent [19]

Hauser

[11] 4,168,699
[45] Sep. 25, 1979

[54] SAMPLING CATHETER
[75] Inventor: Thomas M. Hauser, St. Paul, Minn.
[73] Assignee: Mentor Corporation, Minneapolis, Minn.
[21] Appl. No.: 822,702
[22] Filed: Aug. 8, 1977
[51] Int. Cl.$^2$ ............................................. A61M 25/00
[52] U.S. Cl. ................................. 128/768; 128/349 R
[58] Field of Search .............................. 128/348–351, 128/2 B, 2 W, 2 M

[56] References Cited
U.S. PATENT DOCUMENTS

| | | | |
|---|---|---|---|
| 2,212,334 | 8/1940 | Wallerich | 128/349 R X |
| 3,058,472 | 10/1962 | Thornton | 128/348 |
| 3,108,595 | 10/1963 | Overment | 128/350 R |
| 3,938,530 | 2/1976 | Santomieri | 128/349 R |
| 4,023,559 | 5/1977 | Gaskell | 128/2 W |
| 4,043,346 | 8/1977 | Mobley et al. | 128/349 R |

OTHER PUBLICATIONS

Newman, et al., "Double Lumened Catheterization of Ileal Conduit"—Bockley—Univ. Minnesota Press, 1974.

*Primary Examiner*—Dalton L. Truluck
*Attorney, Agent, or Firm*—Kinney, Lange, Westman & Fairbairn

[57] ABSTRACT

A sampling catheter having an outer tube of resilient material with a normally closed distal end and an inner flexible tube which is longer than the outer tube and which is normally held in retracted position with respect to the distal end of the outer tube by means of a loop of the inner tube which is fastened to the outer tube. The assembled catheter is disposed in a sealed package with the inner tube in such retracted position.

8 Claims, 6 Drawing Figures

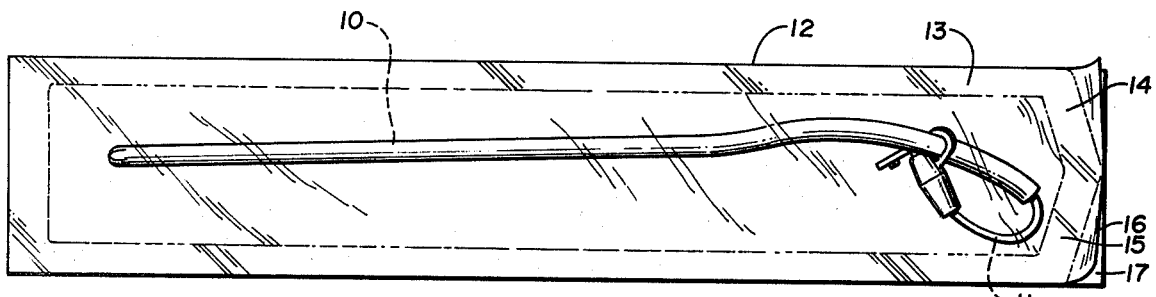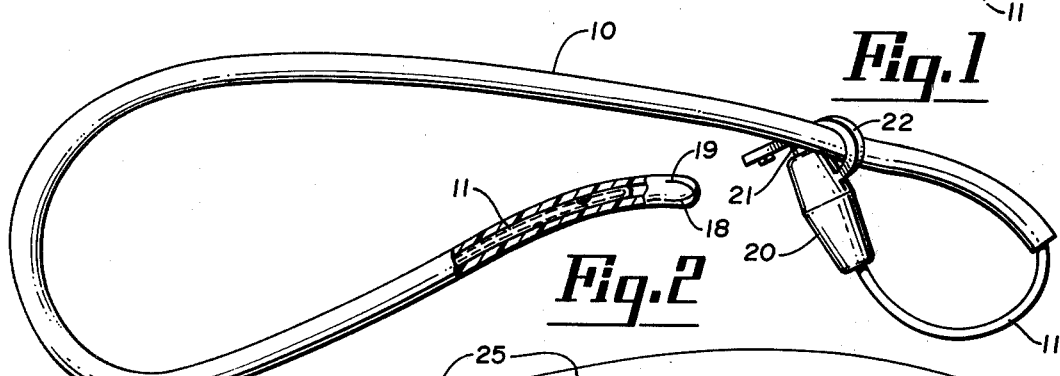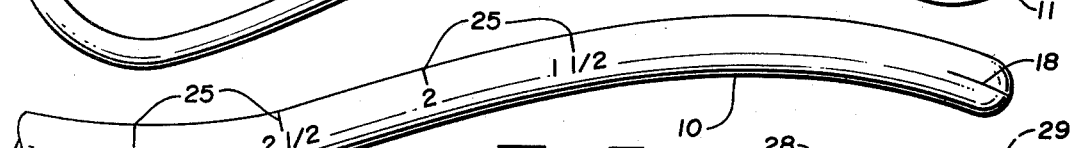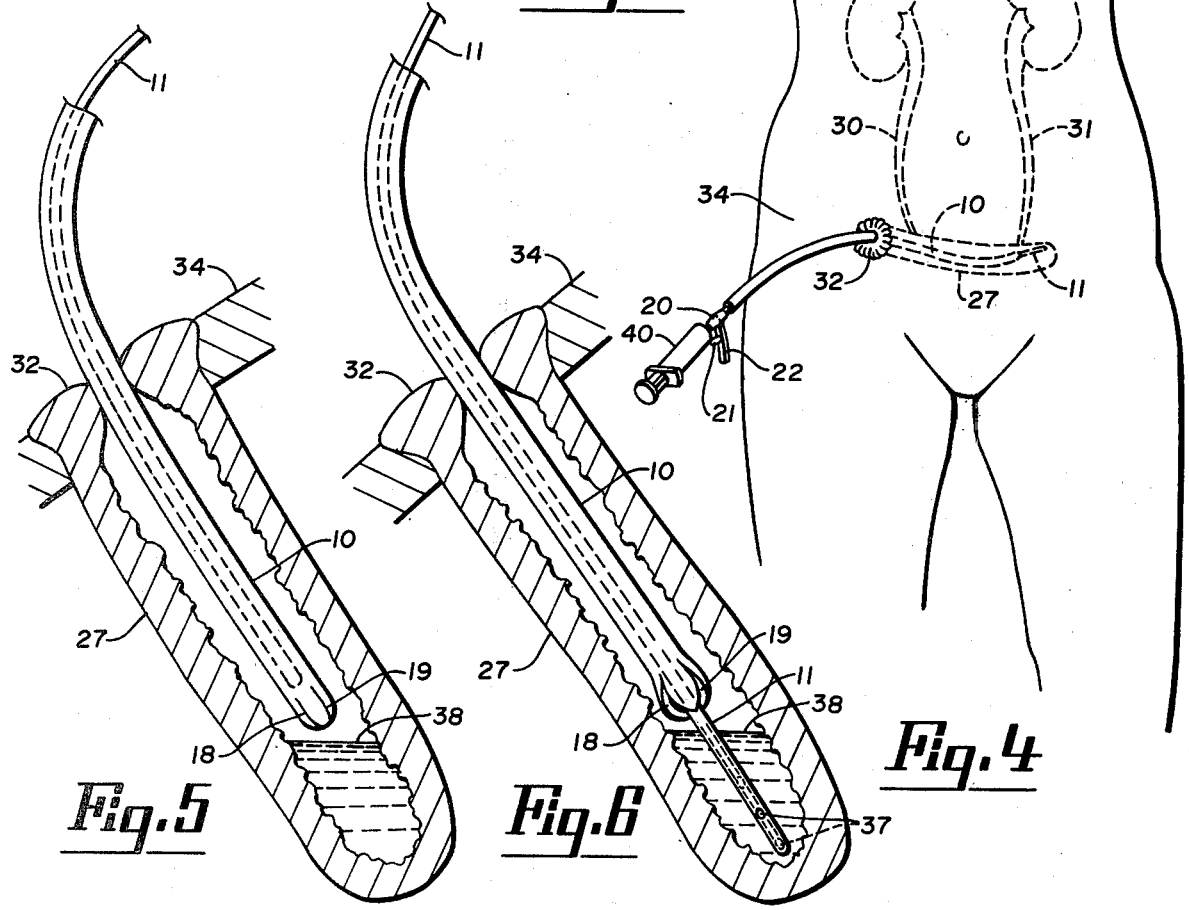

4,168,699

SAMPLING CATHETER

BACKGROUND OF THE INVENTION

It is very important in connection with any catheter arrangement for withdrawing a sample of body fluid to ensure that the sample is not contaminated in any way. Customarily, the catheter is a flexible tube of some kind which is inserted into the body cavity and fluid is withdrawn through this tube. The opening to the body cavity is often contaminated with bacteria and the tube, in being inserted through the opening, accumulates bacteria which in turn are introduced into the specimen being withdrawn.

In order to overcome this, it has been proposed to use an inner tube which is maintained in retracted position while the outer tube is being inserted into the body cavity. When it is desired to take the sample, a suitable collection means such as a syringe is attached to the inner tube and the inner tube is moved forwardly into the body cavity. Since the inner tube is spaced from the distal end of the outer tube while the latter is being inserted into the body cavity, it is possible to keep the inner tube relatively free from contact with bacteria. The problem with such an arrangement is that if the distal end of the outer tube being inserted into the body cavity is open, a certain number of bacteria are forced into the end of the outer tube and these can, in turn, be collected by the inner tube as the inner tube is forced forwardly through the distal end of the outer tube. While it has been proposed to have the distal end of the outer tube which is inserted into the body made so that it is normally closed and is opened only when the inner tube is shoved forwardly, there is a problem in connection with preventing contamination of the inner tube from other sources than that of the body cavity. In order for the inner tube to be able to be moved forwardly beyond the distal end of the outer tube, it is necessary to have the inner tube substantially longer than the outer tube. This raises a danger that the inner tube can be accidentally withdrawn from the outer tube. Even though the inner tube may be packaged with the major length thereof already disposed in the outer tube, a portion of the inner tube inevitably projects beyond the proximal end of the outer tube and raises the possibility of the inner tube being withdrawn completely in the course of removing the catheter from the package. For example, if the assembled catheter is disposed within a package, as is normally the case, a nurse opening the package may instinctively pull the inner tube out since it is already projecting a substantial distance out of the outer tube. Once she does this, it is very likely that the inner tube will be contaminated before it is placed back in the outer tube. This may result in not only contaminating the sample, but may also cause infections to be introduced into the patient when the inner tube which has been handled by the nurse is inserted through the normally closed end of the outer tube into the body cavity.

The problem of avoiding contamination of the sample when drawing the same is particularly important in connection with ileac diversions in which the ureters from the bladder are connected directly to a section of the ileum, forming an ileal conduit, which in turn has a restricted open end extending through a cavity of the abdominal wall. Normally, a collection bag is attached to the ileal conduit through a suitable fitting and the urine passing out through the opening or stoma of the ileal conduit is collected in the bag. When it is desired to take a sample of the urine within the ileal conduit, a tube is inserted so that it extends through the stoma into the ileal conduit. It is obvious that, with such an arrangement, the presence of bacteria within the stoma is very great and, unless some precautions are taken to avoid contamination of the collection tube by the bacteria present along the walls of the stoma, a contaminated urine sample will be obtained.

SUMMARY OF THE PRESENT INVENTION

The present invention is concerned with a catheter in which there is an outer tube and an inner tube, the outer tube having a normally closed distal end through which the inner tube can be moved and in which there is means for maintaining the inner tube prior to use in a relatively fixed position with respect to the outer tube in which the distal end of the inner tube is spaced inwardly from the normally closed distal end of the outer tube.

A further feature of the present invention is that the inner tube is provided with means for holding the inner end looped about and fastened to the outer tube.

A further feature of the present invention is that the outer tube has indicia thereon to indicate the extent to which the outer tube has been inserted into a body cavity.

A further feature of the present invention is that the proximal end of the inner tube has a fitting for enabling the coupling with said inner tube of a syringe to enable the withdrawal through said inner tube of a sample of body fulid. The means for detachably securing the inner end of a loop of the inner tube to the outer tube includes a detachable closure for the opening in such fitting and a strip for holding the detachable closure, the strip being wrapped around the outer tube prior to need for use of the catheter, to retain the inner tube in the fixed withdrawn position.

The present catheter is particularly designed for use in connection with an ileac diversion for the withdrawal of a urine specimen therefrom.

A further feature of the invention is that the amount of the inner tube projecting from the proximal end of the outer tube is sufficiently limited that this portion never extends beyond the distal portion of the outer tube so that any handling of this portion projecting from the proximal end of the outer tube does not result in any contamination being introduced into the body passage.

Further objects and features of the invention will be apparent from a consideration of the accompanying specification, claims and drawing.

BRIEF DESCRIPTION OF THE DRAWING

FIG. 1 is a plan view of my improved catheter in a sealed package;

FIG. 2 is a plan view, partly in section, on a somewhat larger scale showing the catheter outside of the sealed package and with the catheter looped back on itself;

FIG. 3 is a fragmentary view on a still larger scale showing the distal portion of the outer tube and showing the indicia thereon to indicate the extent to which the catheter is inserted in the body;

FIG. 4 is a view of a portion of a human body showing in dotted lines the kidneys, the ureters and the ileal conduit together with my improved catheter inserted therein;

FIG. 5 is a sectional view of the ileal conduit with a portion of the catheter shown as inserted therein; and FIG. 6 is a view similar to FIG. 5 but with the inner tube of the catheter projected beyond the distal end of the outer tube into a position in which it can collect the urine sample.

DESCRIPTION OF THE PREFERRED EMBODIMENT

Referring to FIG. 1, the catheter is shown in a sealed package of the type in which it is normally kept until ready for use. It will be noted that it includes an outer tube 10, an inner tube 11, and a sealed container 12. The container 12 may, for example, have a back wall 17 of relatively opaque material such as paper and a front transparent wall 16 of suitable plastic which is sealed to the back wall 17 along sealing areas 13 around the periphery of the container. Adjacent one end, the transparent wall 16 is sealed to the back wall 17 along inclined sealing areas 14 and 15 which leave a tab portion which can be grasped to separate the transparent front wall 16 from the back wall 17. While the particular form of package is not new with applicant, the combination with the other elements of the catheter is important as far as the present invention is concerned.

As best shown in FIG. 2, the outer or distal end of outer tube 10 is provided with a pair of slits 18 and 19 which are disposed transversely with respect to each other. The distal end of outer tube 11 through which slits 18 and 19 extend is normally closed and remains closed despite the slits 18 and 19. These slits, however, define petal portions which can be displaced by movment of the inner tube through the distal end of the outer tube, as is shown in FIG. 6 and as will be presently explained.

The inner tube 11 is preferably provided with a fitting 20 designed to facilitate the connection of a syringe or similar device to the tube 11. The fitting 20 is provided with a cylindrical passage therethrough communicating with the interior of tube 11 and having an outer opening designed to receive the end of the syringe, as best shown in FIG. 4. The open end of fitting 20 opposite to that to which the inner tube 11 is connected is normally closed by a closure member 21 which is connected to the fitting 20 by a flexible strap or strip 22, as best shown in FIG. 2. The flexible strap 22 and the closure member 21 operate to provide a means for sealing the end of the fitting 20 and prevent the access of foreign matter therein. They also provide a means for holding the tube 11 in a desired position with respect to the outer tube 10. As will be noted from the sectional portion of the view of FIG. 1, the inner tube 10 has its distal end within and slightly spaced from the distal end of the outer tube 10. By looping the inner portion of the inner tube 11 about the inner end of the outer tube 10 and fastening it there, it is assured that the distal end of the tube 11 will remain within the outer tube 10 while the catheter is being handled preparatory to insertion into the body cavity and during the time of such insertion. Furthermore, the fact that the tube 11 is fastened to the outer tube by the fitting 20, the strap 22 and the closure member 21, makes it less likely that the inner tube 11 will accidentally be withdrawn upon opening of the package 12. Unless the tube 11 is fastened in this manner, there is a tendency for the nurse or other attendant in unwrapping the package 12 to pull out the inner tube 11, thus exposing it to contamination.

It is also to be noted that the proximal portion of tube 11 projecting beyond the proximal end of the outer tube 10 up to the fitting 20 is much less than the length of outer tube 10 so that there is no danger that any portion of the inner tube 11 projecting beyond the proximal end of tube 10 will ever be inserted into the body cavity.

A further feature of the invention is that I have provided indicia 25 along the outer portion of the outer tube 10. It will be noted that the indicia "1½", "2", "2½", and "3" appear. These indicia are intended to represent inches from the distal end of tube 10 and serve to indicate how far the tube 10 has been inserted. The patient's chart can show how far the tube should be inserted and these indicia thus act as a guide to facilitate proper insertion of the outer tube 10. Obviously, the indicia may be in any suitable units of measurement and may extend for any distance along the outer tube 10.

In FIG. 4, I have shown a somewhat diagrammatic showing of a body in which there has been an ileac diversion. The ileac conduit is represented by the reference numeral 27. It will be noted that it is connected in communication with the two ureters 30 and 31 which in turn lead from the kidneys 28 and 29. The urine from the kidneys 28 and 29 drains through the ureters 30 and 31 to the ileal conduit 27. As best shown in FIGS. 5 and 6, the ileal conduit 27 is secured to the abdominal wall 34 by a neck portion 32 providing a stoma through which urine can pass and which provides for the insertion of a catheter when it is desired to collect a urine sample. Normally, a bag or other suitable urine collecting device is secured by a suitable fitting to the stoma 32.

When it is desired to take a sample of urine, the bag or other urine collecting device is removed and the area around the stoma is cleansed and treated with a suitable antiseptic. The catheter is then grasped with tweezers and inserted through the stoma into the ileal conduit 27. During this action, it is preferable to allow the loop at the proximal end of inner tube 11 to remain secured to the outer tube 10 as shown in FIGS. 1 and 2. This insures that the distal end of the inner tube 11 will be spaced inwardly from the distal end of the outer tube 10, as is shown in FIG. 5. When the catheter has been inserted the desired distance as shown in FIG. 5, the fitting 20 to which the proximal end of the inner tube 11 is secured can be removed from outer tube 10 by removing the closure member 21 from the opening in the fitting 20. The tube 11 can now be pushed forwardly so that the distal end of the inner tube 11 passes out through the distal end of outer tube 10 causing the various petal portions of the distal end to spread apart as shown in FIG. 6. The inner tube 11 can then be moved inwardly to the approximate position shown in FIG. 6.

As best shown in FIG. 6, the inner tube 11 is provided with a plurality of openings 37 through the sidewall thereof adjacent the distal end. These openings provide for the admission of urine or other fluid to the interior of the tube 11. As shown in FIGS. 5 and 6, it has been assumed that the patient is in an inclined position so that the fluid tends to settle towards the innermost portion of the ileal conduit, the fluid line being indicated by the reference numeral 38. Either after the tube 11 is inserted to the position shown in FIG. 6 or while the inner tube 11 is still in the position shown in FIG. 5, a syringe is attached to the distal end of the tube 11 through the fitting 20. This is done by removing the closure 21 from the proximal end of the fitting 20 and inserting the connection tube of the syringe 40. The syringe 40 should, of course, be a sterile syringe. Care should be taken after removal of the closure member 21 to avoid any contact with the tip of the syringe as it is being inserted into the end of the fitting 20.

With the syringe 20 connected to the inner tube 11, the desired sample can be withdrawn simply by drawing back on the handle of the syringe. If there is any difficulty in withdrawing the urine, the catheter and/or the inner tube 11 may be rotated slightly. Care must be taken, however, not to pinch the catheter in this process. It is usually desirable to remove all of the urine from the conduit. Normally, only a small amount of urine will be obtainable at one time, for example, 2 to 3 ml.

After the sample has been taken, the feeding tube should be retracted so that the distal end of it is well inside the outer tube 10. The entire catheter is then removed from the stoma. Urine is transferred from the syringe to a sterile container, care being taken not to contaminate the specimen during transfer. The stoma area should then be wiped with cotton saturated with soap and water solution, rinsed, the area dried, and the normal collection bag replaced.

It will be seen that with this arrangement, a sample can be taken with practically no chance for any contamination. During insertion of the catheter, the distal end of outer tube 10 is closed and the chances of any bacteria entering the proximal end of the tube 10 are minimal. Due to the novel way in which the tube 11 is retained in a looped condition with respect to the outer tube 10, the distal end of the inner tube 11 is retained within the outer tube 10 until the inner tube 11 is moved forwardly as shown in FIG. 6. At no time does any of the proximal portion of tube 11 which might be contacted by the operator, extend into a portion of the tube in which the distal end of the tube moves. Furthermore, because of the closure 21, the interior of the fitting 20 is prevented from contamination and the syringe 40 may be inserted without the entrance of any foreign matter. Because of the indicia 25, it is possible for the operator to know just how far the outer tube 10 is being inserted into the cavity. As indicated previously, the patient's chart may indicate how far the tube should be inserted. Because of the inner tube 11 being retained with respect to the outer tube 10 up until the time of actual use, there is very little likelihood of the inner tube 11 being accidentally withdrawn from the outer tube 10 prior to use of the catheter.

While the operation of the catheter has been explained in connection with an ileac diversion, it is to be understood that the catheter can be employed in connection with other body openings and, when so employed, has the same advantage of avoiding any contamination of the fluid being withdrawn.

It will be seen that I have provided a catheter in which there is practically no chance of any contamination of the specimen being withdrawn. This is accomplished by the use of a fitting for attachment of a collection device such as a syringe to not only facilitate the attachment of the syringe without any danger of contamination of the interior of the fitting, but also to act as a means for holding the inner tube in the desired position within the outer tube until the outer tube has been inserted through the opening to the body cavity.

While I have shown a specific embodiment of my invention, it is to be understood that the scope is limited solely by that of the appended claims.

I claim:

1. A sampling catheter comprising:
   an outer tube of resilient material having a proximal open end, and a normally closed distal end, said normally closed distal end having a plurality of portions biased together into engagement with each other but movable apart upon pressure being applied to the interior walls thereof, said normally closed distal end enabling the insertion of said outer tube into a body cavity while minimizing the introduction into said tube of contaminating matter, and
   an inner flexible tube disposed within said outer tube so as to be longitudinally movable with respect thereto and capable of being withdrawn completely therefrom, said inner tube having an overall length greater than the length of said outer tube, the distal end of said inner tube being normally in an inner position in which it does not engage the closed distal end of said outer tube but effective when said inner tube is moved toward said distal end of said outer tube to cause said portions of said closed distal end to move apart to allow the passage therebetween of the distal end of said inner tube, said inner tube having means for guarding against the withdrawal of the inner tube from the outer tube by detachably securing the proximal end of a loop of said inner tube to said outer tube in such a position as to retain said inner tube in a withdrawn position in which the major portion of said inner tube is within said outer tube but in which said outer end is spaced inwardly from the closed outer end of said outer tube.

2. The catheter of claim 1 in which the normally closed distal end of said outer tube has a plurality of transverse slits to form said plurality of portions biased together.

3. The catheter of claim 1 in which the outer tube has indicia thereon to indicate the extent to which the outer tube has been inserted into a body cavity.

4. The catheter of claim 1 in which the proximal end of the inner tube has a fitting for enabling the coupling with said inner tube of a syringe to enable the withdrawal through said inner tube of a sample of body fluid.

5. The catheter of claim 4 in which the means for detachably securing the proximal end of a loop of said inner tube to said outer tube comprises a detachable closure for the opening in said fitting and a strip for holding said detachable closure, which strip is wrapped around said outer tube prior to use of said catheter to retain said inner tube in said withdrawn position.

6. The catheter of claim 1 in which said outer tube is designed for passage through the stoma of an ileac diversion for the withdrawal of a urine specimen therefrom.

7. The catheter of claim 1 in which there is a package which encloses the inner and outer tubes with the inner tube in said withdrawn position.

8. The catheter of claim 1 in which the proximal portion of said inner tube extending out of the outer tube is relatively short as compared with the length of said outer tube so that said proximal portion is never in the same section of said outer tube as is the distal portion of said inner tube which is moved beyond the distal end of the outer tube into the body cavity.

* * * * *